(12) United States Patent
Lee (10) Patent No.: US 11,432,991 B2
(45) Date of Patent: Sep. 6, 2022

(54) CHEST WALL OSCILLATION SYSTEM WITH DIGITAL AUSCULTATION

(71) Applicant: KONINKLIJKE PHILIPS N.V., Eindhoven (NL)

(72) Inventor: Seunghyun Lee, Valrico, FL (US)

(73) Assignee: Koninklijke Philips N.V., Eindhoven (NL)

( * ) Notice: Subject to any disclaimer, the term of this patent is extended or adjusted under 35 U.S.C. 154(b) by 86 days.

(21) Appl. No.: 16/098,573

(22) PCT Filed: May 11, 2017

(86) PCT No.: PCT/EP2017/061405
§ 371 (c)(1),
(2) Date: Nov. 2, 2018

(87) PCT Pub. No.: WO2017/194713
PCT Pub. Date: Nov. 16, 2017

(65) Prior Publication Data
US 2019/0142686 A1    May 16, 2019

Related U.S. Application Data

(60) Provisional application No. 62/334,476, filed on May 11, 2016.

(51) Int. Cl.
*A61H 9/00* (2006.01)
*A61B 7/00* (2006.01)
(Continued)

(52) U.S. Cl.
CPC ........... *A61H 9/0078* (2013.01); *A61B 7/003* (2013.01); *A61H 1/00* (2013.01); *A61H 23/006* (2013.01);
(Continued)

(58) Field of Classification Search
CPC .. A61H 9/0078; A61H 23/04; A61H 23/0245; A61H 1/00; A61H 31/00;
(Continued)

(56) References Cited

U.S. PATENT DOCUMENTS 5,165,417 A * 11/1992 Murphy, Jr. ........... A61B 7/003
                                                                  181/126
6,030,353 A    2/2000 Van Brunt
(Continued)

FOREIGN PATENT DOCUMENTS

WO     WO9103981 A1    4/1991
WO     WO2007106804 A2    9/2007
(Continued)

*Primary Examiner* — Colin W Stuart
*Assistant Examiner* — Douglas Y Sul
(74) *Attorney, Agent, or Firm* — Daniel H. Brean; Andrew M. Gabriel (57) ABSTRACT

Described is a wearable device configured to oscillate a chest of a user. The wearable device may include a chest wall oscillator, a sound detector, and a controller for controlling operations of the chest wall oscillator, based on sound from the sound detector. The chest wall oscillator may be mounted on the chest of the user to oscillate the chest of the user. The sound detector may detect the sound from the chest of the user before, during, and/or after operation of the chest wall oscillator. The controller may change one or more of a frequency, intensity, or duration of the oscillations of the chest wall oscillator, depending on an analysis of the sound from the sound detector.

16 Claims, 6 Drawing Sheets

(51) Int. Cl.
*A61H 23/02* (2006.01)
*A61H 23/00* (2006.01)
*A61H 23/04* (2006.01)
*A61H 1/00* (2006.01)
*A61H 31/00* (2006.01)
*A61B 5/00* (2006.01)

(52) U.S. Cl.
CPC ......... *A61H 23/02* (2013.01); *A61H 23/0245* (2013.01); *A61H 23/04* (2013.01); *A61H 31/00* (2013.01); *A61B 5/0051* (2013.01); *A61H 2201/165* (2013.01); *A61H 2201/1619* (2013.01); *A61H 2201/1621* (2013.01); *A61H 2201/1623* (2013.01); *A61H 2201/1626* (2013.01); *A61H 2201/5005* (2013.01); *A61H 2201/5043* (2013.01); *A61H 2201/5097* (2013.01); *A61H 2205/084* (2013.01); *A61H 2230/405* (2013.01)

(58) Field of Classification Search
CPC .................. A61H 23/006; A61H 23/02; A61H 2201/1623; A61H 2201/1619; A61H 2201/1621; A61H 2201/1626; A61H 2201/165; A61H 2201/5005; A61H 2201/5043; A61H 2201/5097; A61H 2205/084; A61H 2230/405; A61H 2201/0157; A61H 2201/5007; A61H 2201/5056; A61H 2201/5058; A61B 7/003; A61B 5/0051
See application file for complete search history.

(56) References Cited

U.S. PATENT DOCUMENTS

| | | | |
|---|---|---|---|
| 6,036,662 A | 3/2000 | Van Brunt | |
| 6,058,932 A | 5/2000 | Hughes | |
| 6,116,241 A * | 9/2000 | Huygen | A61B 7/003 128/203.14 |
| 6,887,208 B2 | 5/2005 | Botbol | |
| 6,974,425 B2 | 12/2005 | Rogers | |
| 7,785,280 B2 | 8/2010 | Kivisto | |
| 8,192,381 B2 | 6/2012 | Nozzarella | |
| 8,257,288 B2 | 9/2012 | Hansen | |
| 8,460,223 B2 | 6/2013 | Huster | |
| 8,517,016 B2 | 8/2013 | Caro | |
| 8,663,138 B2 | 3/2014 | Huster | |
| 10,702,166 B1 * | 7/2020 | Freeman | A61B 5/08 |
| 2002/0183642 A1 * | 12/2002 | Murphy | A61B 8/00 600/532 |
| 2003/0130588 A1 | 7/2003 | Kushnir | |
| 2004/0162510 A1 * | 8/2004 | Jayne | A61H 31/005 601/41 |
| 2005/0033198 A1 * | 2/2005 | Kehyayan | A61B 7/003 600/586 |
| 2008/0000477 A1 * | 1/2008 | Uster | A61B 5/01 128/204.23 |
| 2008/0108914 A1 | 5/2008 | Brouqueyre | |
| 2008/0281219 A1 * | 11/2008 | Glickman | A61M 16/0051 600/533 |
| 2011/0125068 A1 | 5/2011 | Hansen | |
| 2013/0267877 A1 * | 10/2013 | Van Brunt | A61H 9/0078 601/149 |
| 2013/0289456 A1 * | 10/2013 | Chang Guo | A61H 9/0078 601/149 |
| 2015/0005588 A1 * | 1/2015 | Herken | A61B 7/04 600/301 |
| 2016/0000640 A1 * | 1/2016 | Lai | A61H 9/0078 601/149 |
| 2016/0095792 A1 | 4/2016 | Shockley | |
| 2016/0278663 A1 * | 9/2016 | Freeman | A61B 7/005 |

FOREIGN PATENT DOCUMENTS

| | | | | |
|---|---|---|---|---|
| WO | WO-2010071919 A1 * | 7/2010 | | A61H 31/00 |
| WO | WO2013182944 A1 | 12/2013 | | |

* cited by examiner

CHEST WALL OSCILLATION SYSTEM WITH DIGITAL AUSCULTATION

CROSS-REFERENCE TO RELATED APPLICATIONS

This patent application claims the priority benefit under 35 U.S.C. § 119(e) of U.S. Provisional Application No. 62/334,476 filed on May 11, 2016, the contents of which are herein incorporated by reference.

BACKGROUND OF THE INVENTION

Therapy using pharmacologic medication and a high frequency chest wall oscillation (HFCWO) device (also known as a high frequency chest compression (HFCC) device), are known to alleviate a compromised airway clearance. Therapy using HFCWO devices are known to remove excess mucus and phlegm that collect in the lungs and to treat a variety of diseases, such as cystic fibrosis, emphysema, asthma, hypoxemia, hypercapnia, neuromuscular conditions, bronchiectasis, chronic bronchitis, pneumonia, and other pulmonary disorders. Chest oscillation therapy may be prescribed for acute cases, including to improve bronchial drainage in organ transplant patients and to treat patients susceptible to pneumonia in intensive care and post-surgical units.

Some HFCC devices can be set by the user (e.g. a patient) or respiratory therapist (e.g. a physician) to change, for example, the frequency, and/or intensity of compressions. For optimization of the settings used in the therapy treatment, respiratory therapists typically choose to use a chest wall oscillator at default settings or by following the manufacturers' guidelines. Due to suboptimal use of chest wall oscillators, users continue to be troubled by infections, breathing problems, and other complications of the lungs.

SUMMARY OF THE INVENTION

The present disclosure generally relates to an improved HFCC or HFCWO apparatus and a method for operating the same. The improved HFCC or HFCWO apparatus may be a wearable device that may be configured to oscillate a chest of a user. In some embodiments, the wearable device may include a chest wall oscillator, a sound detector, a controller, a power supply, a remote device, and an article of clothing.

The chest wall oscillator may be configured to be mounted on the chest of the user and to oscillate the chest of the user. The chest wall oscillator may include one or more oscillating elements.

The sound detector may be configured to detect sound from the chest of the user and to output signals corresponding to the sound. The sound detector may comprise a plurality of sound detection elements. The sound detection elements may be positioned to come in contact with different regions of the chest of the user.

The controller may be configured to receive the output signals from the sound detector, and it may be further configured to generate output signals based on the output signals from the sound detector. The output signals of the controller may be communicated to the chest wall oscillator to control one or more of a frequency of oscillations, intensity of oscillations, and duration of a therapy output by the chest wall oscillator.

It is yet another aspect of one or more embodiments of the present disclosure to provide a method of improving the effectiveness of a chest wall oscillator (e.g. an HFCC or HFCWO device). The method may include a process for detecting chest sound at a sound detector of the chest wall oscillator. The method may also include a process for characterizing the detected chest sound at one or more processors of the chest wall oscillator. The method may also include a process for controlling one or more of a frequency, intensity, or duration of oscillations of the chest wall oscillator based on the characterized chest sound.

It is yet another aspect of one or more embodiments of the present disclosure to provide a wearable device configured to oscillate a chest of a user and comprising a chest wall oscillation means for oscillating the chest of the user, sound detection means for detecting sound from the chest of the user and outputting signals corresponding to the detected sound, and control means for receiving the output signals from the sound detection means. The control means may comprise a processing means for generating output signals based upon the output signals from the sound detection means, the output signals of the processing means being communicated to the chest wall oscillation means to control one or more of a frequency of oscillations, intensity of oscillations, or duration of a therapy output by the chest wall oscillation means.

DETAILED DESCRIPTION OF THE EMBODIMENTS

Various example embodiments will be described more fully hereinafter with reference to the accompanying drawings, in which some example embodiments are shown. The present disclosure may, however, be embodied in many different forms and should not be construed as limited to the example embodiments set forth herein. These exemplary embodiments are just that examples and many implementations and variations are possible that do not require the details provided herein. It should also be emphasized that the disclosure provides details of alternative examples, but such listing of alternatives is not exhaustive. Furthermore, any consistency of detail between various examples should not be interpreted as requiring such detail it is impracticable to list every possible variation for every feature described herein.

The language of the claims should be referenced in determining the requirements of the invention. In the drawings, the sizes and relative sizes of layers and regions may be exaggerated for clarity. Like numerals refer to like elements throughout.

It will be understood that, although the terms first, second, third, etc. may be used herein to describe various elements, these elements should not be limited by these terms. These terms are used to distinguish one element from another. Thus, a first element discussed below could be termed a second element without departing from the teachings of the present disclosure. As used herein, the term "and/or" includes any and all combinations of one or more of the associated listed items.

It will be understood that when an element is referred to as being "connected," "contacting," or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular example embodiments only and is not intended to be limiting of the present disclosure. As used herein, the singular forms "a," "an," and "the" are intended to include the plural forms as well, unless the context clearly indicates otherwise. It will be further understood that the terms "comprises," "includes," "including," and/or "comprising," when used in this specification, specify the presence of stated features, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
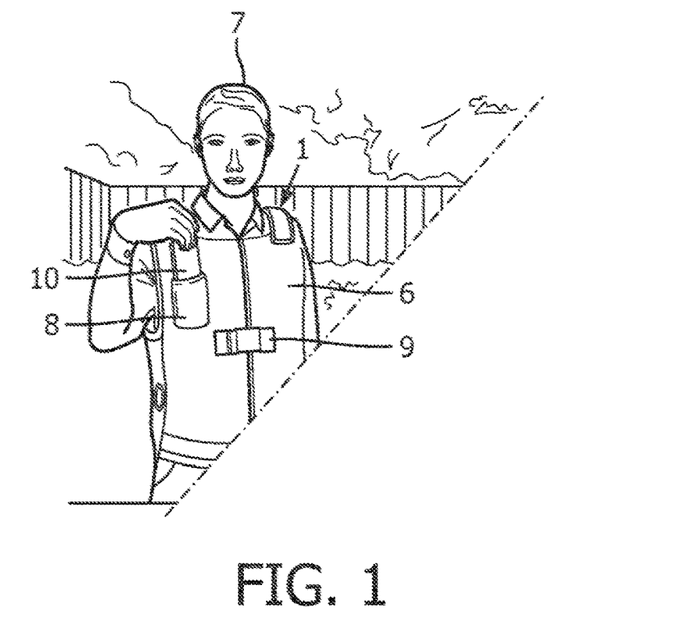
FIG. 1 illustrates a perspective view of a wearable device mounted on a user for providing oscillations to a user, according to some embodiments.

FIG. 1 is a perspective view of a user 7 wearing a wearable device 1 in accordance with one embodiment of the present disclosure. FIG. 1 also depicts a remote controller 10 that is configured to control the wearable device 1.

Figure 2:
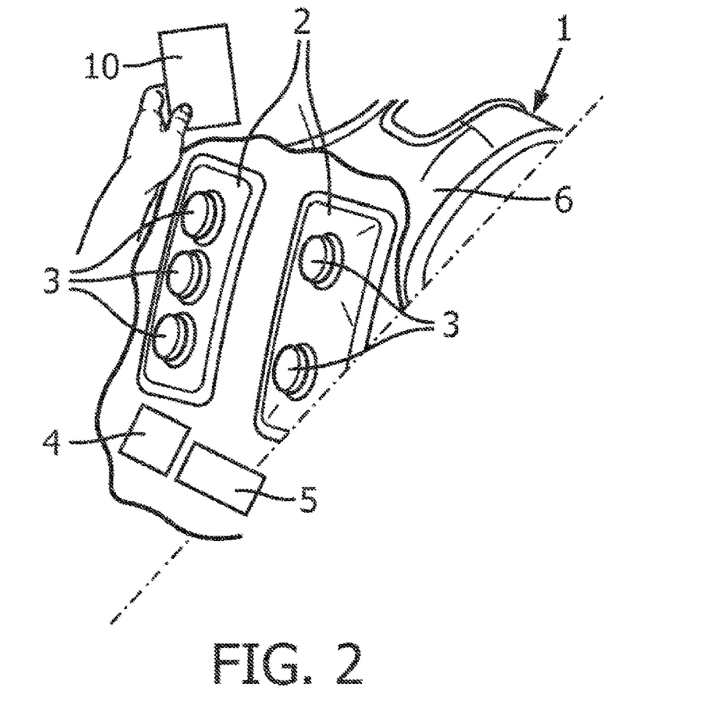
FIG. 2 is a perspective view of the wearable device with an embedded chest wall oscillator and exemplary auscultation system, according to some embodiments.

FIG. 2 depicts a view illustrating various components of the wearable device 1, according to embodiments of the present disclosure. In particular, FIG. 2 illustrates chest wall oscillator 2 (e.g. an HFCWO device), sound detector 3, controller 4, power supply 5, article of clothing 6, and remote controller 10. The chest wall oscillator 2 may be mounted on the chest of the user 7.

The controller 4 of the wearable device 1 may receive output signals from one or more lung sound detectors 3 to thereby control operation settings of the chest wall oscillator 2. The chest wall oscillator 2, when driven by the power supply 5 and according to a configuration of the controller 4, applies a force or forces (e.g. compression, vibration, and/or percussion) to a thoracic region of the body. The remote controller 10 may be external to the wearable device 1 and configured to receive data output from the controller 4. The remote controller 10 may also be configured to control the controller 4.

The wearable device 1 may be suitable for use in a hospital or healthcare facility or for an outpatient at a home. The wearable device 1 may also be suitable for ambulatory use. The article of clothing 6 of the wearable device 1 may be a medical vest, apron, or other suitable garment. The article of clothing 6 may be comprised of various pockets 8 and pouches (not shown) to at least temporarily or permanently incorporate one or more various elements such as the chest wall oscillator 2, sound detector 3, controller 4, power supply 5, and remote controller 10. The article of clothing 6 may also include various straps, zippers, linings, apertures (e.g. for ventilation), and layers, and it may be adjustable by one or more buckles 9 for a secure fit to the torso of the body (e.g. to be held tight around the chest and/or the back). The article of clothing 6 may be made of a suitable fabric for durability and to inhibit odors and/or bacterial growth.

The chest wall oscillator 2 of the wearable device 1 may in some embodiments be positioned in the front of the article of clothing 6 (e.g. a vest) to make direct contact with the chest wall of the user. In other embodiments, the chest wall oscillator 2 may interact with a back of the user. In yet other embodiments, the chest wall oscillator with oscillating elements (described below) may be provided on both the front and back of a vest 6. The chest wall oscillator 2 may fully, or at least mainly, transmit a force to the user's body (e.g. to specific lobes of the lungs). The direction of the force may, in some embodiments, be substantially perpendicular to the user's body. The user may be a human or other animal.

Figure 3:
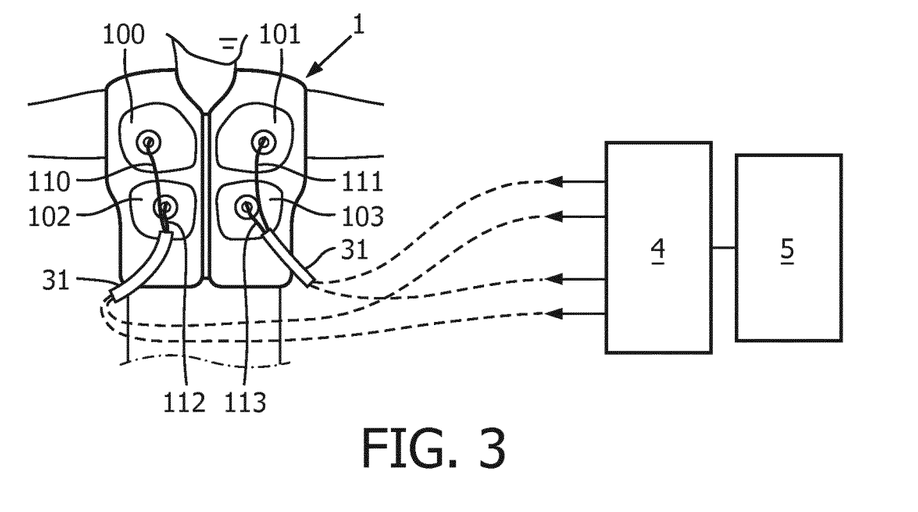
FIG. 3 illustrates an example embodiment of the wearable device having a chest wall oscillator with four oscillating elements as it may be driven by a controller and power supply.
Figure 4:
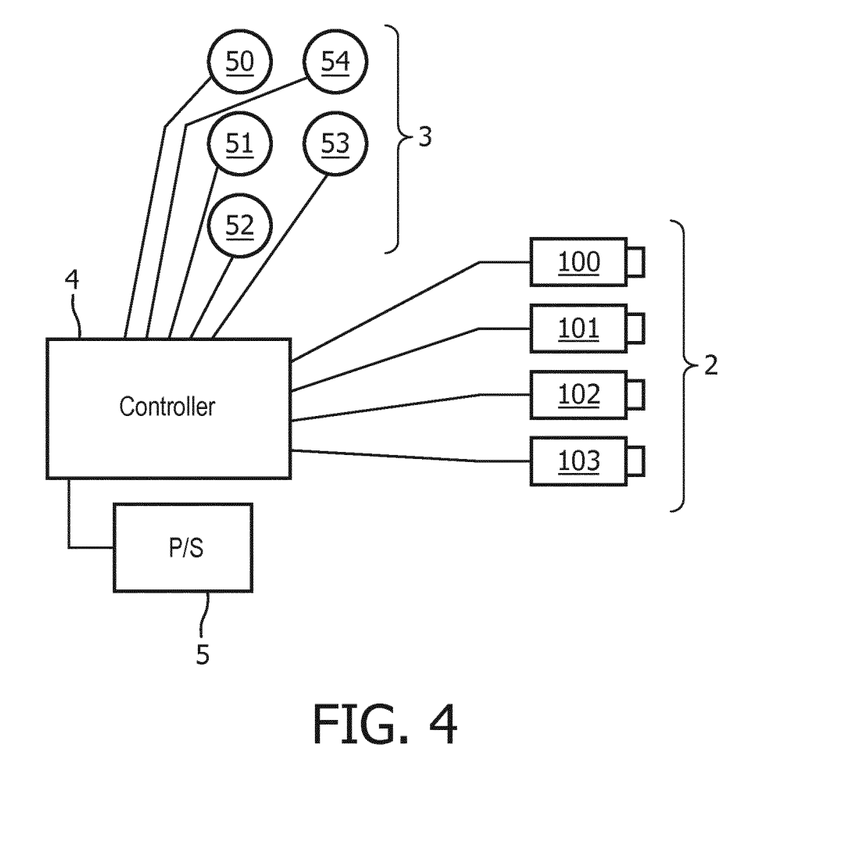
FIG. 4 illustrates a schematic of the wearable device, according to some embodiments.

In some embodiments, the chest wall oscillator 2 of the wearable device 1 may comprise a plurality of oscillating elements. In a non-limiting example, four oscillating elements 100, 101, 102, and 103 may be used, as shown in FIGS. 3 and 4. Each oscillating element (e.g. 100, 101, 102, or 103) may be a bladder (e.g. air-filled), actuator, solenoid, piezoelectric mechanism, electrically actuated hammer, or other compressive or impact device that may provide oscillations to the chest of the user.

The oscillations of the oscillating elements may be driven by a combination of the controller 4 and power supply 5, as shown in FIGS. 3 and 4. The power supply 5 may be an electrical power supply for at least facilitating operation of the controller 4. Additionally, the power supply 5 may receive power by another source (e.g. pneumatically, by a conventional device having a rotary valve, or by any other suitable means). The controller 4 and power supply 5 for the oscillations may in some embodiments be contained within the article of clothing 6, as shown in FIG. 2, and in other embodiments either or both may be contained outside of the article of clothing 6, as shown in FIG. 3. For example, in embodiments where the oscillating elements are air-filled bladders, part of the power supply 5 may be an external compressor, air pulse generator, or blower.

In embodiments where part or all of the power supply 5 is external to the wearable device 1, the power supply 5 may connect to the wearable device 1 through connectors 31. In these example embodiments, part (e.g. a compressor 5) of the power supply may be mounted onto a back of the wearable device 1 or it may be a stand-alone, external unit (e.g. rolled on wheels, fixed, or able to be carried by hand). In example embodiments, where each oscillating element is a solenoid, actuator, or other electrical impact device, the power supply 5 may be entirely electrical. In the example embodiments where the oscillating elements are electrically driven, the power supply 5 may be a rechargeable battery and additionally or alternatively the power supply 5 may be from a standard outlet operating at about 100-265 VAC with a frequency of about 50-60 Hz.

The oscillations or vibrations of the chest wall oscillator 2 may be driven as repetitive, focused pulsations or as compressions on the user's body. The controller 4 may individually configure each oscillating element of the chest wall oscillator 2 to vibrate at a different frequency (e.g. between 0 Hz and 25 Hz, between 5 Hz and 20 Hz, etc.), at a different intensity, and for a different duration. As shown in FIG. 3, the controller 4 may drive each connecting line for each oscillating element (e.g. oscillating elements 100, 101, 102, and 103) with a different (or substantially similar) pulsation. The power supply 5 may also be individually connected to the controller 4 and each oscillating element. In embodiments where the oscillating elements are electrically powered, lines 110, 111, 112, and 113 may be wires or fiber optic channels. In embodiments where the oscillating elements are driven by a compressor, the lines 110, 111, 112, and 113 may be tubes or hoses.

In some embodiments, there may be feedback signals from the oscillating elements of the chest wall oscillator 2. For example, there may be some feedback as to the amount of resistance, pressure change, or force applied by one or more oscillating elements (e.g. solenoids, actuators, or air bladders) during its stroke, which is sent to the controller 4. The controller 4 may therefore know if there is an oscillating element that is not applying a proper force to the chest of the user 7, e.g. for not being in proper contact with the chest. The controller 4 may be able determine the effectiveness of each oscillating element, based on changing sounds from the sound detector 3 and/or the forces applied by each oscillating element, to then make adjustments either manually or algorithmically.

The wearable device 1 as a whole may be effectively used in a comprehensive therapeutic method that takes into account the lung sounds of the user. Breath sounds may be abnormal in certain pathological conditions of the airway or lungs of the user. For example, wheezes are typical in bronchitis, asthma, and emphysema.

Wheezes may be musical and high-pitched hissing sounds normally heard on both expiration and inspiration. A wheezing sound may be characterized by various parameters, such as its location in the lungs, intensity, pitch, duration in the respiratory cycle, and in its relationship to the phase of respiration. The dominant frequency of wheezes is usually between 80 Hz and 500 Hz, and the duration is typically longer than 100 milliseconds (ms).

Crackles are nonmusical and brief sounds heard more commonly on inspiration. They may be classified as fine or coarse. Crackles may be further characterized by various parameters, such as their loudness, pitch, duration, number, timing in the respiratory cycle, location, pattern from breath to breath, and change after a cough or shift in position. Crackles may sometimes be heard at the anterior lung bases after a maximal expiration or after prolonged recumbence.

The sound detector 3 of the wearable device 1 may be configured to optimally sense all of the adventitious lung sounds on both inspiration and expiration in low (e.g. 100 to 300 Hz), middle (e.g. 300 to 600 Hz), and high (e.g. 600 to 1200 Hz) frequency bands. The sound detector 3 may sense adventitious sounds that can be continuous (e.g. wheezes) and discontinuous (e.g. crackles). The sound detector 3 may also detect other adventitious lung sounds, such as rhonchi, stridor, pleural rub, and mediastinal crunch, as these sounds may typically also indicate a pulmonary disorder.

In some embodiments, the sound detector 3 may be a plurality of sound detection elements, as shown in FIGS. 2 and 4. The sound detector 3 (e.g. microphones and/or stethoscopes) of the wearable device 1 may detect the efficacy of the chest wall oscillation therapy. For example, a front end of a diaphragm and condenser microphone may be placed toward a chest of the user. Front ends of the sound detection elements may therefore be positioned closely to particular regions of each lung of the user. In a non-limiting example, sound detector 3 may comprise five sound detection elements 50, 51, 52, 53, and 54, and 55, as shown in FIGS. 2 and 4. In these examples, sound detection element 50 may be coupled to a right upper lobe, sound detection element 51 may be coupled to a left upper lobe, sound detection element 52 may be coupled to a right middle lobe, sound detection element 53 may be coupled to a right lower lobe, and sound detection element 54 may be coupled to a left lower lobe of the user. The number and the location of the sound detection elements may therefore vary to cover more or less of the lung shape, depending on the level of precision needed by the controller 4 implementing computer aided lung sound analysis (CALSA). For example, more than a dozen or even 100 sound detection elements may be used.

The sound detector 3 provides an auscultation function for the controller 4 of the wearable device. In some embodiments, the sound detector 3 may be digital. In these or other embodiments, the sound detection elements of the sound detector 3 may comprise one or more stethoscopes and/or microphones. Where microphones are used, the one or more microphones may be one or more (or a combination) of a diaphragm and condenser microphone, dynamic microphone, ribbon microphone, carbon microphone, piezoelectric microphone, fiber optic microphone, laser microphone, liquid microphone, or microelectromechanical system (MEMS) microphone. The sound detector 3 may optionally be accompanied by an amplifier to amplify the detected sound used by the controller 4.

When digital sound detectors are used, the output signals of the detector may, in some embodiments, be converted to equivalent analog signals. In these embodiments, an analog to digital (A/D) converter may digitize the analog signals for a processor in the controller implementing the computer aided lung sound analysis. In some embodiments the signals may be maintained digitally throughout and in other embodiments an analog auscultation system may be used. Computer aided lung sound analysis (CALSA) techniques may be employed on digitized lung sounds to quantify, characterize, and analyze the various adventitious lung sounds to provide respiratory therapists with a wealth of clinically useful information. For example, a number of crackles per breath cycle (nBC) and a 2-cycle deflection width (2CD) may be calculated and analyzed.

The sound detector 3 may be embedded into the wearable device 1, as shown in FIG. 2. In some embodiments, the placement of the sound detector 3 may be such that no noise from the operation of the wearable device 1 (e.g. a buzzing sound) or any background noise is picked up by the sound detector 3. In these or other embodiments, the controller 4 may also implement filters (e.g. high pass filter, band pass filter, or low pass filter) to isolate the lung sounds from the operation of the chest wall oscillator 2 and/or to filter out background noise. The remote controller 10 may, in some embodiments, control sensitivity settings of the sound detector 3 (e.g. sensitivity of the microphones) to enhance the quality of the detection.

In addition to the adventitious lung sounds being detected, these sounds emanating from within the lungs may be analyzed by the controller 4 implementing CALSA techniques. The sound detector 3 therefore outputs signals, which correspond to the detected sounds, to the controller 4. The controller 4 may receive the output signals and perform an analysis to determine the effectiveness of the therapy. The implementation of CALSA in embodiments of the wearable device 1, disclosed herein, may provide analysis of various parameters, such as the waveform, number, distribution, timing, and pitch of sounds emanating from the user's chest as well as inter-phase characteristics among sound detectors.

Continuous daily monitoring of changes in the lung sounds offers respiratory therapists with earlier indication of a patient's pulmonary health change, providing the respiratory therapist with an opportunity for an early prophylactic intervention to improve overall clinical outcome and patient management. The adventitious lung sounds (e.g. crackles and wheezes) may be monitored before, during, and after chest wall oscillation treatment. Lung sound detection and analysis may be accomplished in the controller 4 of the wearable device 1 and changes to operation settings of the chest wall oscillator 2 may be configured by the controller 4 alone or in conjunction with a remote controller 10.

Figure 5:
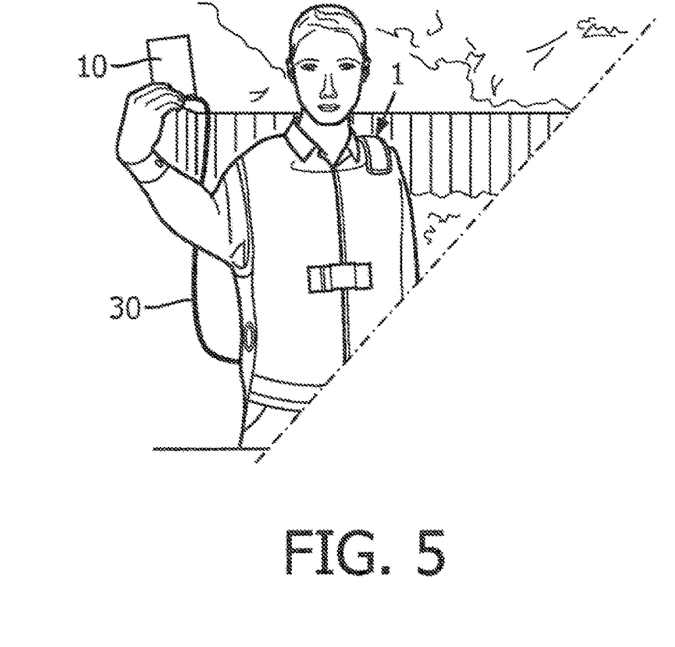
FIG. 5 illustrates an example embodiment of the wearable device where the remote device is hard-wired to a controller of the wearable device.

Referring again to FIG. 1, illustrated therein is the user 7 storing the remote controller 10 into a pocket 8 of the wearable device 1. In some embodiments, the remote controller 10 may be electrically or electromagnetically (i.e. wirelessly) connected to the controller 4 of the wearable device 1. In other words, the connection from the remote controller 10 to the controller 4 may be hard-wired or wireless, but the present disclosure is not so limited. In embodiments where it is hard-wired, an electrical cable or cord 30 may be used to connect the remote controller 10 to the wearable device 1, as shown in FIG. 5. The remote controller 10 may be used for controlling the more specific operations of the chest wall oscillator 2, i.e. by controlling its operation settings, based on the status of the lung sounds as detected by sound detector 3 and analyzed by the controller 4.

Figure 6:
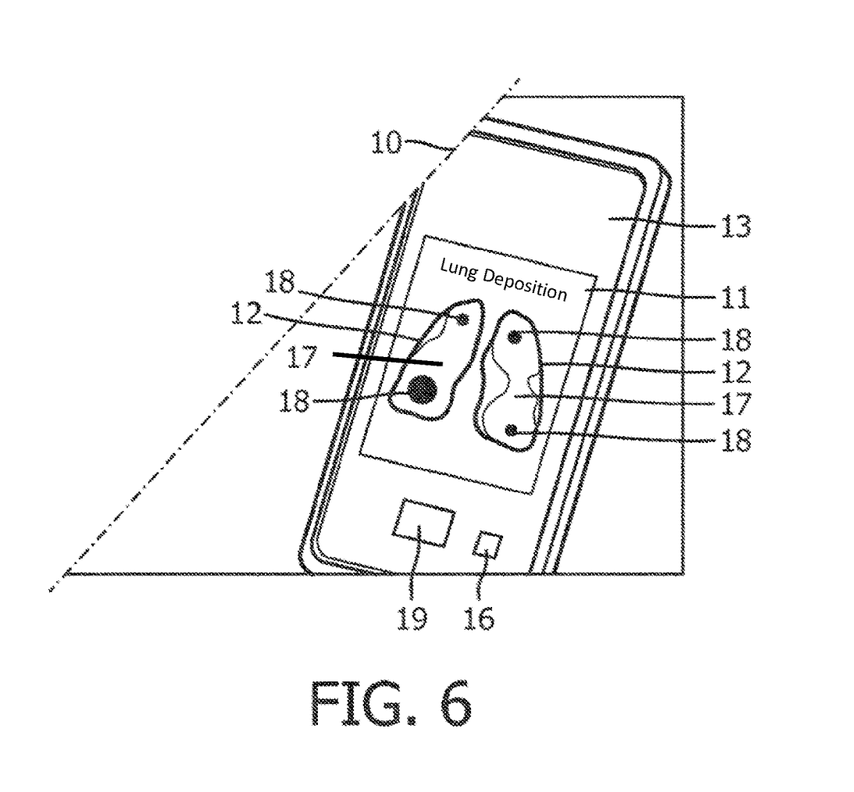
FIG. 6 is a perspective view of exemplary status being displayed from a remote device of the wearable device, according to some embodiments.

FIG. 6 is a perspective view of the remote controller 10, which is operable as an optional remote part of the wearable device 1. The remote controller 10 may be a personal computer (PC), smart phone, tablet, laptop, set-top box (STB), or personal digital assistant (PDA), etc., and it may communicate with the wearable device 1 using any hard-wired standard or a wireless standard (e.g. Bluetooth, WiFi, near field communication (NFC), etc.).

The remote controller 10 is shown in FIG. 6 displaying an example lung deposition status indicator 12 based on the CALSA of output signals from the outputs of the sound detector 3, according to some embodiments. The display of the lung deposition status indicator 12 may be rendered in a status window 11. The status window 11 of the remote controller 10 may form part of a larger user interface display 13 (e.g. a touchpad screen). The status window 11 may specifically display the lung deposition status indicator 12 for one or more regions of each lung, based on sounds detected by the sound detector 3 and as analyzed by the controller 4. For example, the lung deposition status indicator 12 may take the form of a pictorial representation of the lungs, as shown in FIG. 6. An interpretation of the CALSA parameters in such embodiment may translate to lighter or darker shaded regions of lung deposition depicted on the pictorial representation of the lungs of status indicator 12. For example, a high number of crackles per breath cycle (nBC) and/or a wide 2-cycle deflection width (2CD) may be displayed as darker regions 17, as shown in FIG. 6 whereas lighter regions may demonstrate relatively healthy lungs.

The present disclosure is not so limited and different symbols, shapes, shades, letters, graphs and/or colors may be used to constitute the lung status indicator from the various CALSA parameters, which are described below. Additionally or alternatively, the size or shape of a dark circle 18 on the pictorial status indicator 12 may indicate the level of an applied force to a particular region of the user's chest. The wave, vibration, or oscillation may indicate the level of frequencies optimum for specific lung regions based on the CALSA and extrapolated lung deposition characteristics. A number or other type of symbol may be used to show an operation setting of oscillation control on a user interface of the remote device 10.

The status window 11 may in some embodiments contain a button 19 (e.g. on the touchpad screen) to return to an operation screen 20, discussed below, and another button 16 to alternately parse the CALSA parameters (e.g. in graphs instead of the pictorial lung deposition status indicator 12 representation). The analyzed sounds may therefore be interpreted by the controller 4 (or in the remote controller 10) such that they may be instructively representative of the depositions on the lungs (e.g. mucus and/or phlegm) before an initial operation of the chest wall oscillator 2 and additionally during or after one or more therapy sessions. In other words, before, during, or after a therapy session, status window 11 may visually show the status of the lung analysis based on one or more of the CALSA parameters. The CALSA parameters are characterized from the lung sounds.

Figure 7:
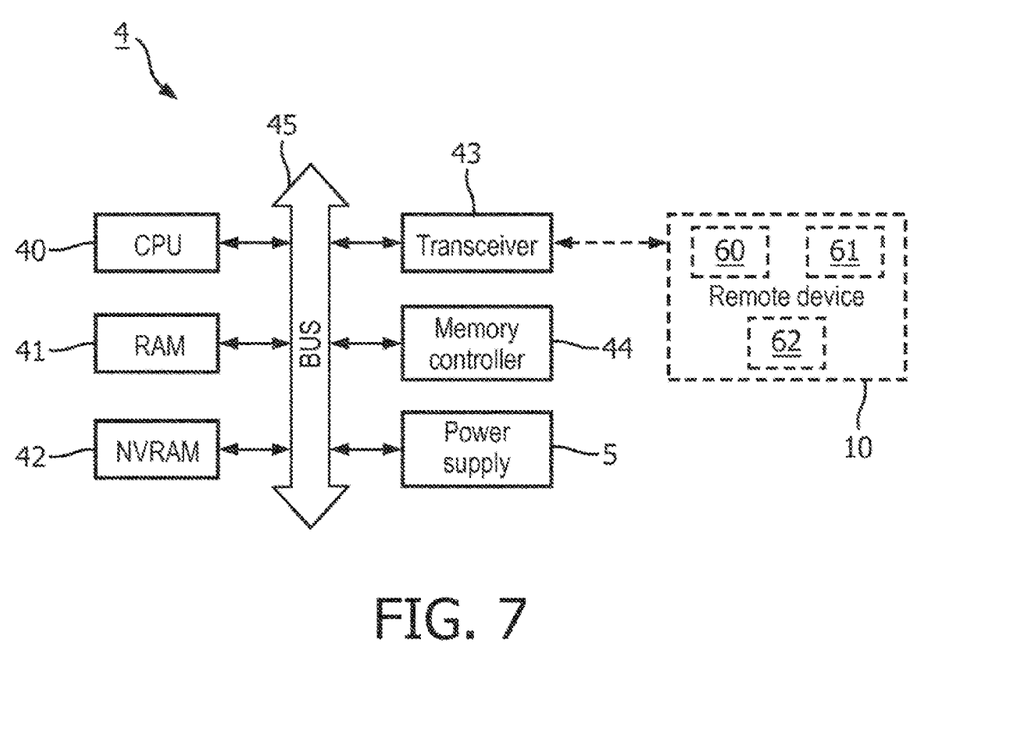
FIG. 7 is an example block diagram of a controller of the wearable device, including some of its external interfaces, according to some embodiments.

Computer-aided analysis is advantageous in its ability to objectively differentiate and quantifiably measure different breath sound patterns. In some embodiments, the breath sound patterns from the lungs may be recorded and stored in a storage medium of the controller 4. For example, the lung sounds and/or the resulting analyzed parameters may be stored in a random access memory (RAM) 41 or in a non-volatile memory (NVRAM) 42, such as a solid-state flash device and/or a magnetic disk drive, as shown in FIG. 7. Computerized acoustic analysis of recorded sounds is advantageous and improves the reliability of detection of all lung sounds when compared to listening manually through an analog stethoscope, which depends on the variable perception by the human ear, acoustic limitations of the stethoscope itself, and subjective characterizations.

The controller 4 of the wearable device 1 may provide not only a means for objective measurement but also a means to evaluate and determine the effectiveness of the therapy. To accomplish this, the controller 4 may comprise one or more processors (e.g. a central processing unit (CPU) 40, as shown in FIG. 7) to receive output signals from the sound detector 3, analyze the output signals, and respond to the analysis. Response to the analysis may be a selection of operation settings and an output of signals corresponding to the selected operation settings. The controller 4 communicates these output signals to the chest wall oscillator 2, as shown in FIG. 4. The remote controller 10 may be configured, in some embodiments, to receive another set of output signals from the controller 4 and to control the output signals of the controller 4 communicated to the chest wall oscillator 2 based on the another set of output signals. The selection itself may therefore be directed manually, for example, by the user 7 operating the remote device 10, or more automatically as determined by a software program being run by a processor (e.g. CPU 40) of the controller 4. The wearable device 1 may then be operated again using the selected operation settings.

The CALSA parameters may be determined and used by the controller 4 to adjust and optimize subsequent therapy settings. The wearable device 1 may therefore be individualized for each user to achieve a maximum, clinical outcome. The therapy being individualized, according to embodiments of the present disclosure, may maximize the efficacy of the treatment and user comfort. For example, the controller 4 may continuously monitor its internally generated CALSA parameters and alert the clinician for an early intervention, such as an adjustment of the settings of the therapy prophylactically. The adjustments may, in some embodiments, be made automatically in an automated fashion. For example, adjustments may be based on the respiratory therapist's predetermined protocol and thus based on certain operating parameters programmed into a memory of the controller 4. The predetermined protocol may form part of one or more algorithms, and the algorithm may be programmed into software, which may be stored in a non-transitory memory (e.g. NVRAM 42) and accessed by one or more processors (e.g. CPU 40) of the controller 4. Optimum therapeutic settings may therefore be identified algorithmically by the controller 4, based on the CALSA parameters. These operation settings may be displayed and controllable on the remote controller 10.

Figure 8:
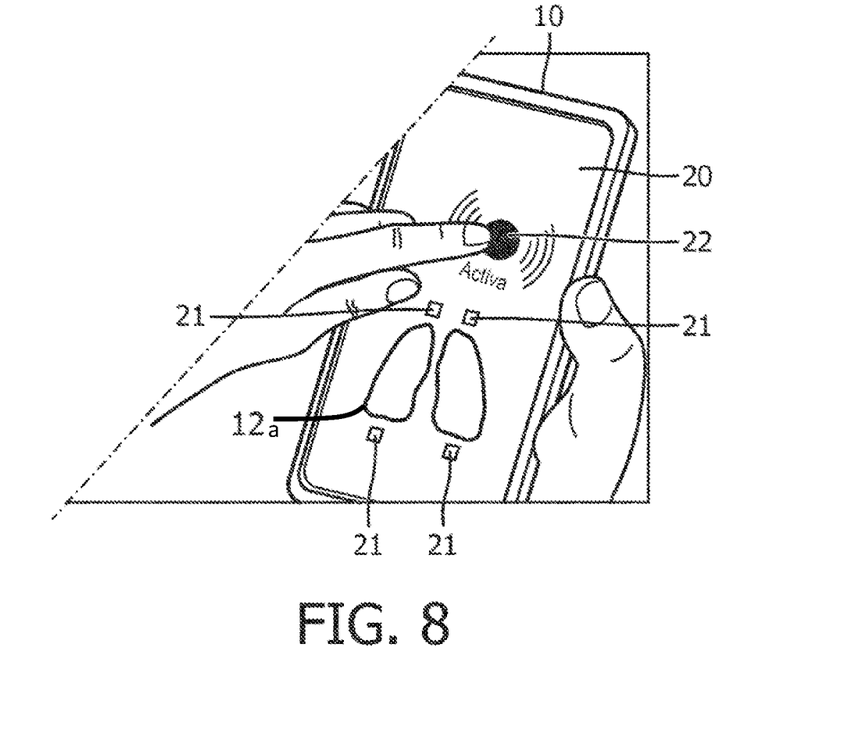
FIG. 8 is a depiction of the remote device operating the wearable device, according to some embodiments.

FIG. 8 illustrates the remote controller 10 of the wearable device 1 displaying an operation screen 20, according to some embodiments. A user interface (e.g. a touchpad screen) on the remote controller 10 may include fields 21 and activation button 22 for specifically operating the controller 4 that may control the chest wall oscillator 2. The operation screen 20 of the remote controller 10 may be operable for custom adjustment of the operation settings of the therapy via fields 21 shown on operation screen 20. For example, the intensity (amplitude) of the pulses generated by the oscillating element, the frequency of the oscillations, the duration of the oscillations, and/or other parameters for each region of each lung 12a may be adjusted to individually control each oscillating element. For example, each of the duration, frequency, and intensity of the oscillations may be increased, decreased, continued at the same level, or the therapy may be terminated.

The adjustments of the operating parameters of the chest wall oscillator 2 may be made individually to each oscillating element, individually for each operation setting, or in some preferable combination. The custom adjustments may preferably and optimally be made by the controller 4 in response to the generated CALSA parameters. The adjustments of the operating parameters may be configured at the controller 4 by the user 7 by changing each field 21 on operation screen 20. Afterwards, the operation of the wearable device 1 may commence by selecting a button on operation screen 20, for example an Activate button 22, as depicted in FIG. 8. The remote device may therefore be able to activate (e.g. turn on) or deactivate (e.g. turn off) the wearable device 1 through the Activate button 22. The user may deactivate the oscillations of the wearable device 1 if, for example, the frequency, duration, or intensity are too great and thus uncomfortable for the user.

Automatic change of the operating parameters of the wearable device 1 may be over a predetermined (e.g. programmed) period of time. For example, in an automated mode the user could start at a desired starting frequency and/or intensity for the chest wall oscillation therapy and automatically gradually increase the frequency and/or intensity over a predetermined (e.g. programmed) period of time to a desired maximum frequency and intensity, based on the CALSA parameters.

A processor 40 of the controller 4, shown in FIG. 7, may transmit efficacy data (e.g. CALSA parameters, described below) and receive through a user interface (e.g. fields 21 on a touchpad of the remote controller 10) operation settings for controlling the operation of the chest wall oscillator 2 through a transceiver 43 of the controller 4. The transceiver 43 may be a wireless transceiver. A processor 60 in the remote controller 10 may similarly have an interface to a transceiver 61 (e.g. a wireless transceiver), as shown in FIG. 7.

A memory component (e.g. RAM 41 and/or NVRAM 42) of the controller 4 or a memory component 62 of the remote controller 10 may store the previous settings of a therapy. The memory component may store one or more pre-programmed therapy modes to allow delivery of chest wall oscillation therapy to a user in accordance with any one of the plurality of pre-programmed therapy modes stored in the memory component. The modes may specify a frequency, intensity, duration, or other parameter for each oscillating element individually. Each oscillating element may vibrate synchronously (e.g. in phase) with the other oscillating elements or asynchronously (e.g. out of phase) with the other oscillating elements. The oscillations may be of different waveform types, such as a square wave, sinusoidal, triangular, or other pulse shape.

The controller 4 may be configured to export (e.g. wirelessly or wired) the characterizations and calculations of the adventitious lung sounds in a non-readable fashion or readable fashion, such as a graph, table, or other suitable chart. CALSA may therefore enhance interpretation of lung sounds and help with diagnosis and management of users suffering from different lung diseases. For example, the lung sounds may be recorded, measured, graphically displayed, analyzed, and the user treated respective to the analyzed results. Analysis of the results and subsequent recommendation of operation settings may be performed by the respiratory therapist or automatically (e.g. by implementation of one or more programmed algorithms) by the controller 4.

Respiratory assessment of the chest oscillator, and the algorithm that implements the optimal selection of the therapy settings may be based on one or more of the CALSA parameters. The one or more of the CALSA parameters may be objectively characterized, for example, numerically represented in graphs and tables or via some visual representation, as shown in FIG. 6. The objective characterizations may be representative of one or more CALSA parameters. The CALSA parameters are at least a calculated breath rate (e.g. number of breaths per minute), nBC, 2CD, duration of crackles (e.g. measured in milliseconds), number of regions with crackles, and an intensity of crackles (e.g. measured in decibels). A score may be assigned to each of these CALSA parameters, for example, if it is well-below average, below average, above average, and well-above average, based on the characterizations. In some embodiments, a low score may be preferable but in others a high score may be preferable. Either the controller 4 or the remote controller 10 of the wearable device 1 may make the scoring determinations.

For example, if a breath rate is below 12 breaths per minute then a lowest score (e.g. 2) may be given, else if the breath rate is below a range of 12 to 14 breaths per minute then a slightly higher score (e.g. 3) may be given, else if the breath rate is above an average between 15 to 18 breaths per minute then a higher score may be given (e.g. 4), or if the breath rate is well-above average with 20 or more breaths per minute then a highest score may be given (e.g. 5).

Similarly, scores may be assigned for the number of measured crackles per breath cycle. For example, a lowest score (e.g. 2) may be assigned for less than 1 crackles per breath, a slightly higher score (e.g. 3) for 2 to 5 crackles per breath, a higher score (e.g. 4) for 6 to 9 crackles per breath, and a highest score (e.g. 5) for 10 or more crackles per breath.

Similarly, scores may be assigned for the number of regions of the lungs determined to have crackles. For example, a lowest score (e.g. 2) may be assigned for less than 1 region with crackles, a slightly higher score (e.g. 3) for 2 to 3 regions, a higher score (e.g. 4) for 4 to 5 crackles per breath, and a highest score (e.g. 5) for 6 or greater regions that have crackles.

Similarly, scores may be assigned for an intensity measurement of the crackles. For example, a lowest score (e.g. 2) may be assigned for an intensity value less than 1, a slightly higher score (e.g. 3) for an intensity value between 2 and 4, a higher score (e.g. 4) for an intensity value between 5 and 8, and a highest score (e.g. 5) for an intensity value greater than 9.

Control by the controller may be based on the assessment score tally, individually on just one parameter, or on a combination of a plurality of parameters. Depending on the assessment score, a frequency, intensity, or duration may be varied in subsequent therapy. For example, a therapy may be driven for 15 minutes once a day, 15 minutes twice a day, 30 minutes twice a day, or 30 minutes four times a day, depending on one or more CALSA parameters as characterized (e.g. measured, analyzed, and/or calculated) by the controller 4 (or remote controller 10). In this example, the duration is incrementally increased, but in other examples the frequency and/or intensity could also or alternatively increase, based on the one or more CALSA parameters. In another non-limiting example, depending on the CALSA parameters (e.g. depending on one or more of the breath rate, nBC number, 2CD width, duration of crackles, number of regions with crackles, or intensity of crackles), a therapy may be first driven at a frequency of 10 Hz, for a duration of 5 minutes, and at an intensity of 6 out of 10 (this may any intensity setting and may be determined at manufacture). After the therapy, the CALSA parameters may then be generated again and then a second therapy may be driven. For example, the second therapy may be driven at an increased frequency of 15 Hz, for an increased duration of 10 minutes, and at an increased intensity of 8 out of 10. As has been stated, not all of the operation settings need to be changed. That is, any one or more of these operation settings may change for each therapy session, based on the CALSA parameters. None of the settings necessarily need to change, though, since in some instances the controller (or remote device) or respiratory therapist may determine based on the lung sound that a second therapy session with the operation settings kept constant is appropriate.

Figure 9:
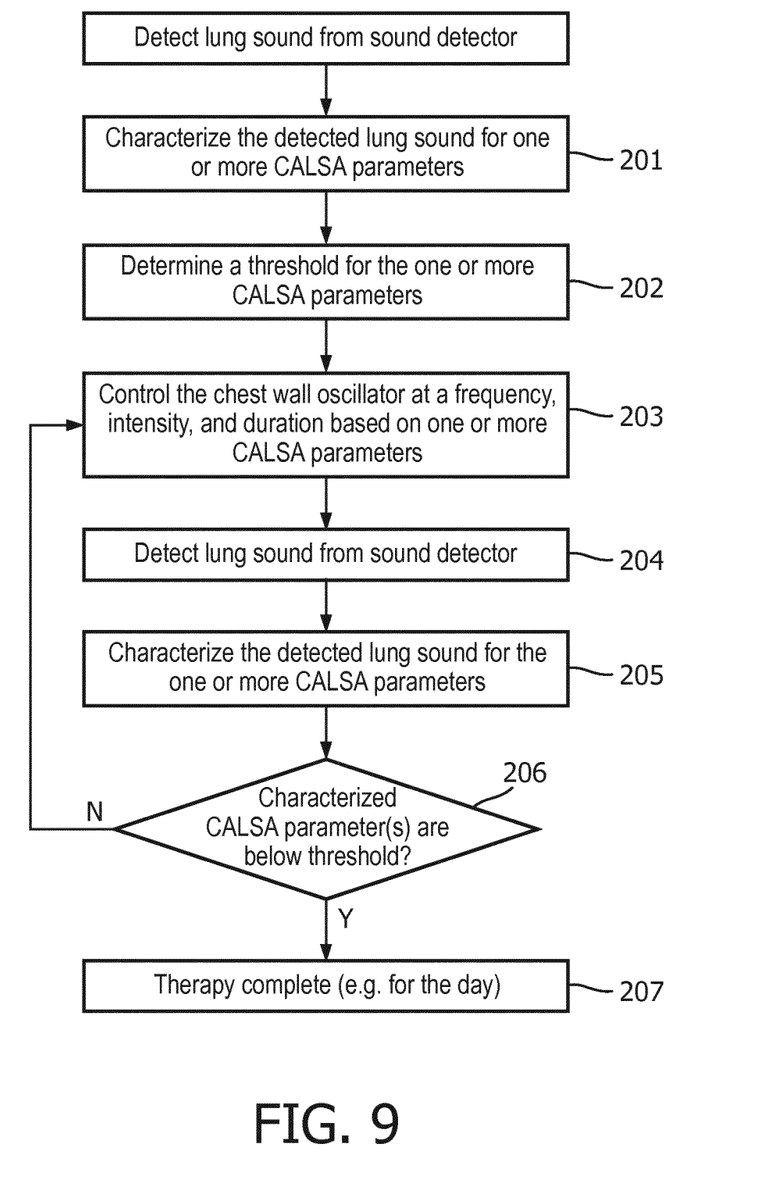
FIG. 9 is a flow chart for describing an example method of using the wearable device, according to some embodiments.

FIG. 9 is a flow chart for describing an example method of using the wearable device, according to some embodiments. The processes of the method presented below are intended to be illustrative. In some embodiments, the method may be accomplished with one or more additional operations not described and/or without one or more of the processes discussed. Additionally, the order in which the processes of the method are illustrated in FIG. 9 and described below is not intended to be limiting. In one embodiment, the processes described below are performed by a device similar to or the same as wearable device 1. In a process, a lung sound may be detected using one or more sound detectors. In the next process 201, the lung sounds may be characterized by calculating one or more of the CALSA parameters.

In process 202, one or more thresholds for one or more of the CALSA parameters may be determined. For example, the one or more thresholds for the one or more CALSA parameters may be individually set at a lowest, low, high, or highest value, depending on a goal of the respiratory therapist or as programmed (algorithmically) into the controller 4. For example, continuing the example given above where a high score of 4 is given for 6 to 9 crackles per breath cycle, the predetermined threshold would be the range of 6 to 9 crackles per breath cycle. In some embodiments, the determination and comparison with a threshold value may be less specific. For example, the threshold value may generally encompass a degree of change in response to a therapy, such as a rate of change, a direction of change, a speed of change, etc., and decisions may be made with respect to the chest wall oscillator accordingly.

In process 203, one or more oscillating elements of the chest wall oscillator 2 may be controlled to oscillate at a first frequency, a first intensity, and a first duration for a first therapy. Next, in process 204, after the first therapy is complete (e.g. at the end of the first duration) or during the therapy itself the lung sounds may be detected again. Then, in process 205, the lung sounds may be again characterized.

In process 206, the new characterized CALSA parameters may be compared against the desired (predetermined) threshold(s). For example, if a desired threshold was set at a high (or low, lowest, or highest) nBC value then a decision can be made based on the results. That is, continuing with the above example, if the actual nBC value is not below the threshold of 6 to 9 crackles per breath cycle (i.e. below the high threshold) then in process 206 a second therapy repeating the cycle begun at process 203 may be determined necessary to perform. In this second therapy, one or more of the operation settings (frequency, intensity, or duration) may change (e.g. increase) from the initial, first therapy. If the one, targeted CALSA parameter or a combination of targeted CALSA parameters (e.g. a tally) was or is now desirably below a threshold then in process 206 a decision may be made to complete the therapy 207. The decision, in other words, to run another therapy session with or without changes to one or more operation settings may be made based on one threshold, a combination of thresholds, or as determined by the tallied assessment scores.

Data on the lung sounds generated in the controller 4 may be stored in a memory (41 or 42) of the controller 4 before being exported to the remote controller 10 for a visual representation of the computer-aided analysis. The data may also be stored in a memory 62 of the remote controller 10, as shown in FIG. 7, before being shared with a respiratory therapist for initial or subsequent analysis. The transmission of the CALSA parameters data to the respiratory therapist (e.g. over the Internet) from the remote controller 10 (and/or to the remote controller 10 from the controller) may be securely accomplished using suitable encryption.

Figure 10:
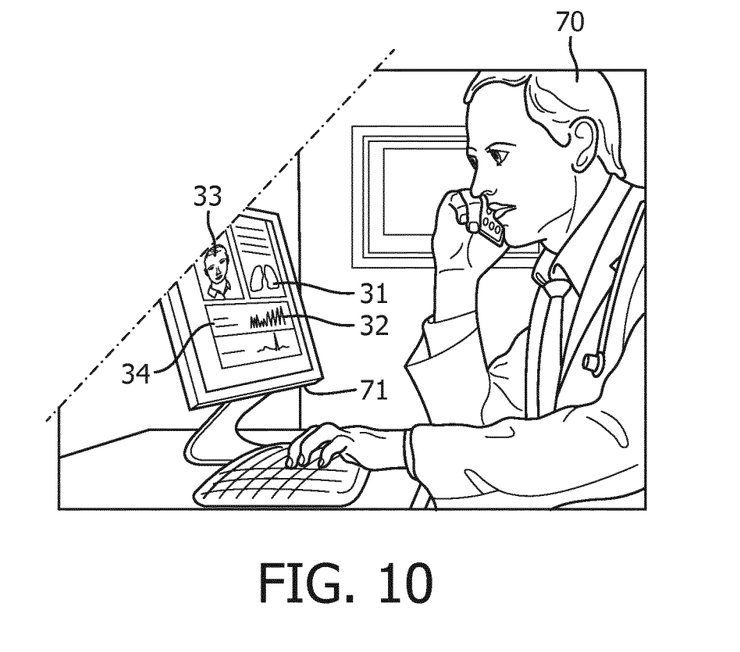
FIG. 10 is a depiction of a clinician reviewing trending lung sound parameters that indicate a high pulmonary risk and discussing analysis results with the patient for prophylactic treatment.

FIG. 10 is a depiction of a clinician 70 reviewing trending respiratory assessment data, such as a number of coughs and a number of crackles 32, including any lung deposition change over a period of time on the order of days, weeks, or months, and providing instructions for manual operation of the wearable device 1, according to some embodiments. The respiratory therapist may provide the instructions, including operation settings, based on the shared information sent to him or her from the remote controller 10. The shared data received at a computer 71 of the respiratory therapist 70 may include settings data 34, which relate to the various operating settings associated with a therapy (e.g. a frequency and intensity settings of a previous therapy for each oscillating element) and also may include information associated with the date and time of the therapy. The numerical representation of the various CALSA parameters may demonstrate the clinical effectiveness of the therapy, including graphs and tables 32, such as the breath rate, nBC, 2CD, duration of crackles, number of regions with crackles, and an intensity of crackles. A computer 71 of the respiratory therapist may also interpret the data to represent the same visual lung deposition status indicator 12 of the lungs shown on the remote controller 10 in window 31. The remote controller 10 may also share to the computer 71 of the respiratory therapist 70 personal information 33 of the user undergoing the chest wall oscillation treatment.

Figure 11:
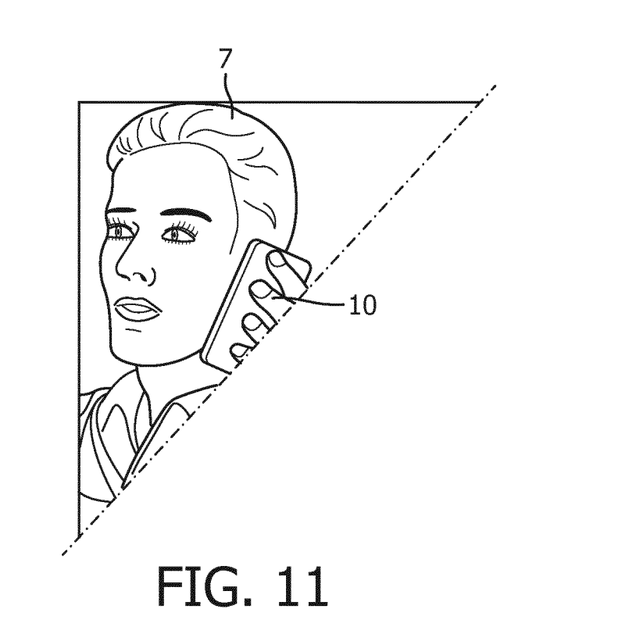
FIG. 11 is a depiction of the user receiving instructions for manual operation of the chest wall oscillator of the wearable device, according to some embodiments.

FIG. 11 is a depiction of a user receiving instructions for manual operation of the wearable device 1, according to some embodiments. Control of operation settings of the controller 4 may be performed via the remote controller 10 by the user and, in some embodiments, as directed by a respiratory therapist.

Returning to FIG. 7, FIG. 7 is a block diagram of the controller 4, illustrating that the controller 4 may be equipped with a processor 40, RAM 41, non-volatile RAM 42, a bus 45, a memory controller 44, a transceiver 43, and interfaces to a power supply 5 and the remote controller 10. The remote controller 10 may similarly be equipped with a processor, RAM, non-volatile memory, a bus, a memory controller, a power supply, and a transceiver, but additionally with an external user interface (e.g. a touchpad screen), as shown in FIGS. 6 and 8.

The various operations and features described and illustrated herein with respect to the controller 4 and the remote controller 10 may be implemented by software, hardware, or any combination thereof. More specifically, the processes and procedures described and illustrated herein may be implemented by the installation of logic corresponding to the processes into a medium such as an integrated circuit, a volatile memory, a non-volatile memory, a magnetic disk, or an optical storage. The processes and procedures described and illustrated herein may also be installed in the form of a computer program and executed by one or more processors.

The controller 4 and/or remote controller 10 of the wearable device 1 may be driven entirely by software running on a processor 40 and/or processor 60, respectively. In some embodiments, the methods described herein may be fully or partially hardware-implemented. For example, a hardware-implemented module may comprise dedicated circuitry or logic that is configured by programmable logic and substantially similar to functionality if implemented by a processor. In these embodiments, the hardware circuit may be an application specific integrated circuit (ASIC) or a field programmable gate array (FPGA).

What is claimed is:

1. A wearable device configured to oscillate a chest of a user, comprising:
   a wearable garment;
   a chest wall oscillator mounted on the wearable garment and configured to be mounted on the chest of the user and to oscillate the chest of the user in a therapy session;
   a sound detector mounted on the wearable garment and configured to detect sound from the chest of the user and to output signals corresponding to the sound; and
   a controller configured to receive the output signals from the sound detector;
   the controller being configured to:
      characterize the output signals of the sound detector as one or more adventitious lung sounds;
      determine, based on the one or more adventitious lung sounds, an efficacy of the therapy session; and
      generate control output signals based upon determination of the efficacy, the control output signals of the controller being communicated to the chest wall oscillator to control one or more of a frequency of oscillations, an intensity of oscillations, and a duration of the therapy session;
   wherein the controller comprises one or more processors configured to characterize the output signals of the sound detector as one or more adventitious lung sounds using computer aided lung sound analysis (CALSA);
   wherein the one or more processors are configured to quantify one or more of a number of crackles per breath cycle (nBC), a 2-cycle deflection width (2CD), a duration of crackles, a number of regions with crackles, or an intensity of crackles; and
   wherein the controller is further configured to increase one or more of the controlled frequency, intensity, or duration from an initial frequency, intensity, and/or duration, respectively, if one or more of the quantified nBC number, 2CD width, duration of crackles, number of regions with crackles, or intensity of crackles is greater than a predetermined threshold;
   wherein the predetermined threshold is one or more of a degree of change, a rate of change, a direction of change, and a speed of change in response to therapy.

2. The wearable device of claim 1, wherein the chest wall oscillator comprises one or more solenoids, actuators, or bladders.

3. The wearable device of claim 1, wherein the chest wall oscillator comprises a plurality of oscillating elements, each oscillating element of the plurality of oscillating elements being operated individually at one or more of a different frequency or intensity.

4. The wearable device of claim 1, wherein the sound detector comprises one or more stethoscopes and/or microphones.

5. The wearable device of claim 1, wherein the sound detector comprises five sound detection elements, the five sound detection elements being positioned to come in contact with a right upper lobe, left upper lobe, right middle lobe, right lower lobe, and left lower lobe, respectively, of the user.

6. The wearable device of claim 1, wherein the wearable garment comprises a wearable vest configured to carry the chest wall oscillator and the sound detector.

7. The wearable device of claim 6, wherein the wearable vest is further configured to carry the controller and a power supply.

8. The wearable device of claim 1, further comprising a remote controller configured to receive another set of output signals from the controller and to control the control output signals of the controller based upon the another set of output signals.

9. The wearable device of claim 1, wherein the controller is further configured to change one or more of the controlled frequency, intensity, or duration responsive to comparison of one or more of the quantified nBC number, 2CD width, duration of crackles, number of regions with crackles, or intensity of crackles to the predetermined threshold.

10. A method of operation of a chest wall oscillation system, comprising:
oscillating, with a chest wall oscillator mounted on a wearable garment, a chest of a user in a therapy session;
detecting sound at a sound detector mounted on the wearable garment;
characterizing the detected sound at one or more processors of the chest wall oscillation system as one or more adventitious lung sounds;
determining, based on the one or more adventitious lung sounds, an efficacy of the therapy session; and
controlling, based on the determining, one or more of: a frequency of the chest wall oscillator, an intensity of the chest wall oscillator, and a duration of the therapy session;
wherein the characterizing comprises quantifying one or more of a number of crackles per breath cycle (nBC), a 2-cycle deflection width (2CD), a duration of crackles, a number of regions with crackles, or an intensity of crackles; and
wherein the controlling includes increasing one or more of the frequency, intensity, or duration from an initial frequency, intensity, and/or duration, respectively, if one or more of the quantified nBC number, 2CD width, duration of crackles, number of regions with crackles, or intensity of crackles is greater than a predetermined threshold;
wherein the predetermined threshold is one or more of a degree of change, a rate of change, a direction of change, and a speed of change in response to therapy.

11. The method of claim 10, wherein the chest wall oscillator comprises a plurality of solenoids, actuators, or bladders, each of the plurality of solenoids, actuators, or bladders being operable at a different frequency or intensity.

12. The method of claim 10, wherein the sound detector comprises a plurality of sound detection elements, the plurality of sound detection elements detecting the sound from different regions.

13. The method of claim 10, wherein the controlling of the chest wall oscillator is partly or entirely performed by a remote controller.

14. The method of claim 10, wherein the controlling changes one or more of the controlled frequency, intensity, or duration responsive to comparison of one or more of the quantified nBC number, 2CD width, duration of crackles, number of regions with crackles, or intensity of crackles to the predetermined threshold.

15. A wearable device configured to oscillate a chest of a user, comprising:
chest wall oscillation means of a wearable garment for oscillating the chest of the user in a therapy session;
sound detection means of the wearable garment for detecting sound from the chest of the user and outputting signals corresponding to the detected sound;
control means for receiving the output signals from the sound detection means, the control means comprising a processing means for characterizing the output signals of the sound detection means as one or more adventitious lung sounds, determining based on the one or more adventitious lung sounds an efficacy of the therapy session, and generating control output signals based upon determination of the efficacy, the control output signals of the processing means being communicated to the chest wall oscillation means to control one or more of a frequency of oscillations, an intensity of oscillations, and a duration of the therapy session;
wherein the control means comprises one or more processors configured to characterize the output signals of the sound detector as one or more adventitious lung sounds using computer aided lung sound analysis (CALSA);
wherein the one or more processors are configured to quantify one or more of a number of crackles per breath cycle (nBC), a 2-cycle deflection width (2CD), a duration of crackles, a number of regions with crackles, or an intensity of crackles; and
wherein the control means is further configured to increase one or more of the controlled frequency, intensity, or duration from an initial frequency, intensity, and/or duration, respectively, if one or more of the quantified nBC number, 2CD width, duration of crackles, number of regions with crackles, or intensity of crackles is greater than a predetermined threshold;
wherein the predetermined threshold is one or more of a degree of change, a rate of change, a direction of change, and a speed of change in response to therapy.

16. The wearable device of claim 15, wherein control means is configured to change one or more of the controlled frequency, intensity, or duration responsive to comparison of one or more of the quantified nBC number, 2CD width, duration of crackles, number of regions with crackles, or intensity of crackles to the predetermined threshold.

* * * * *